(12) United States Patent
Hogan

(10) Patent No.: US 7,319,782 B2
(45) Date of Patent: Jan. 15, 2008

(54) REAL-TIME IMAGING AND ANALYSIS SYSTEM

(76) Inventor: Josh N. Hogan, 620 Kingswood Way, Los Altos, CA (US) 94022

( * ) Notice: Subject to any disclaimer, the term of this patent is extended or adjusted under 35 U.S.C. 154(b) by 748 days.

(21) Appl. No.: 10/870,120

(22) Filed: Jun. 17, 2004

(65) Prior Publication Data

US 2004/0257581 A1 Dec. 23, 2004

Related U.S. Application Data

(60) Provisional application No. 60/479,811, filed on Jun. 18, 2003.

(51) Int. Cl.
*G06K 9/00* (2006.01)
*A61B 5/05* (2006.01)
*A61B 6/00* (2006.01)

(52) U.S. Cl. ............... 382/128; 382/103; 382/141; 600/316; 600/407; 600/476

(58) Field of Classification Search ............ 382/103, 382/128–134, 141–154; 600/103, 104, 160–166, 600/316, 407, 425, 473, 476–478
See application file for complete search history.

(56) References Cited

U.S. PATENT DOCUMENTS

| | | | | |
|---|---|---|---|---|
| 3,700,801 A | * | 10/1972 | Dougherty | 348/169 |
| 4,902,128 A | * | 2/1990 | Siebecker et al. | 356/152.1 |
| 5,867,604 A | * | 2/1999 | Ben-Levy et al. | 382/254 |
| 6,307,951 B1 | * | 10/2001 | Tanigawa et al. | 382/103 |
| 6,615,072 B1 | * | 9/2003 | Izatt et al. | 600/478 |
| 6,728,571 B1 | * | 4/2004 | Barbato | 600/478 |
| 7,139,078 B2 | * | 11/2006 | Hogan | 356/480 |
| 7,248,907 B2 | * | 7/2007 | Hogan | 600/316 |
| 2003/0130562 A1 | * | 7/2003 | Barbato et al. | 600/109 |
| 2004/0260158 A1 | * | 12/2004 | Hogan | 600/316 |
| 2005/0018203 A1 | * | 1/2005 | Hogan | 356/480 |
| 2006/0063985 A1 | * | 3/2006 | Hogan | 600/310 |
| 2006/0063989 A1 | * | 3/2006 | Hogan | 600/316 |

* cited by examiner

*Primary Examiner*—Bhavesh M Mehta
*Assistant Examiner*—Manav Seth (57) ABSTRACT

A sub-surface imaging system includes a broadband set of coherent beams with low divergence angle. It further includes an optical processing system which provides a probe and a reference beam, applies the probe beam to the target to be analyzed, recombines the beams interferometrically and varies the relative temporal relationship of the coherence phase of the two beams at a frequency compatible with video display rates. It further includes control and processing systems.

95 Claims, 6 Drawing Sheets

REAL-TIME IMAGING AND ANALYSIS SYSTEM

CROSS REFERENCES TO RELATED APPLICATIONS

This application claims priority from provisional application Ser. No. 60/479,811 filed on Jun. 18, 2003.

FIELD OF USE

The invention relates to real-time imaging and analysis and in particular to sub-surface imaging and analysis at video rates.

BACKGROUND

In a typical imaging and analysis systems a target is scanned in two dimensions by a probe signal. A corresponding detected signal provides information about the scanned points in the target which can then be displayed as an image and analyzed visually or by electronic processing.

Real-time imaging consists of repeatedly scanning, detecting and displaying the resulting images at a sufficiently high rate to observe changes in the target scanned as the changes actually occur and to avoid motion related analysis issues.

For real-time scanning and display, one dimension of the image must be scanned and displayed at high speed. For example, in a typical video system the high speed dimension is referred to as the horizontal scan rate, while the lower scan rate dimension is referred to as the vertical rate.

Real-time non-invasive imaging is a powerful technique for non-destructive imaging or quantitative analysis of a variety of targets including, semiconductor wafers, materials, human tissue, etc. The analysis can include scanning for defects, discontinuities, or in the case of tissue, abnormalities such as malignant growths.

Real-time imaging is particularly valuable in the case of in vivo analysis of human tissue, where non-destructive, non-invasive sub-surface scanning allows convenient analysis of potentially abnormal tissue without the need for a costly, time consuming and invasive biopsy.

The two dimensional scanning of real-time imaging systems typically consists of a high speed scan along one axis and a low speed scan along an orthogonal direction. A typical video rate imaging system requires a high speed scanning rate of the order of 15 KHz and low speed scan of the order of 30 Hz, providing a progressive scan image rate of 30 images per second. These rates are typically sufficiently high, with respect to the motion speeds, to support in vivo display of tissue without blurring motion artifacts.

There are existing scanning technologies suitable for low speed scanning. These include electromechanical based technologies, such as galvanometers or moving coils actuators. However, these technologies are not suitable for high speed scanning. Existing high speed scanning electromechanical technologies include rotating polygons which are expensive and physically large and in addition have significant alignment issues.

High scanning rates can also be achieved by acousto-optic scanning where an optical beam is deviated by a chirped acoustic wave propagating through a crystal. The acoustic wave is generated by applying an RF signal to the crystal by means of a transducer. The RF signal has a repetitive and linearly varying frequency which provides a matching linearly varying frequency (chirp) to the acoustic wave. The acoustic wave intercepts the optical wave and deviates it by an angle proportional to the RF frequency. This technique allows high speed scanning, however, it is expensive, requires significant RF power because the angular deviation is small, and the system is physically large.

One or more of these aspects of high speed moving parts, high cost components, high power consumption and large physical size make existing scanning systems unsuitable for cost effective, compact, robust, high speed imaging systems.

A typical sub-surface imaging technology, such as confocal microscopy, can generate tomographic images for example of tissue, containing information similar to biopsy sections by scanning a one dimensional array, parallel to the surface of the tissue (x-scan), at varying depths (z-scan) in tissues. The series one dimensional scans at various depths can be displayed as a single tomographic image. Such imaging systems, however, have many of the undesirable aspects described above.

Another sub-surface imaging technology, optical coherence tomography, can also generate tomographic, biopsy-like images. Such systems use a super-luminescence diode (SLD) as the optical source. The SLD output beam has a broad bandwidth and short coherence length. Optical coherence tomography involves splitting the output beam into a probe and reference beam. The probe beam is applied to the system to be analyzed (the target). Light scattered or reflected back from the target is combined with the reference beam to form the measurement signal.

Because of the short coherence length only light that is scattered from a depth within the target such that the total optical path lengths of the probe and reference are equal combine interferometrically. Thus, the interferometric signal provides a measurement of the scattering value at a particular depth within the target. By varying the length of the reference path length, a measurement of the scattering values at various depths can be measured and in this manner, the z-axis can be scanned. The reference path length is typically varied by physically moving a reflecting mirror.

In order to get the biopsy-like image, the second dimension scan (the x-scan) is obtained by translating the probe focusing mirror parallel to the target surface. However, at least some of the above mentioned limitations apply to this imaging method also and, in general, these limitations represent a barrier to applying current imaging technologies to compact, cost effective real-time applications.

There is therefore an unmet need for a cost effective, compact, robust, high speed scanning technology that has no moving parts and that is compatible with imaging systems.

SUMMARY OF THE INVENTION

The invention provides a method, apparatus and system for sub-surface imaging and analysis. The invention includes a broadband set of coherent beams with low divergence angle. It further includes a signal processing system which provides a probe and a reference beam, applies the probe beam to the target to be analyzed, recombines the beams interferometrically and varies the relative temporal relationship of the coherence phase of the two beams. It further includes control and processing systems.

DETAILED DESCRIPTION OF THE INVENTION

A novel imaging and analysis system is illustrated in and described with reference to FIG. 1, where a real-time imaging system is shown. It includes two generators 101 and 106, each of which generates a set of repetitive discrete coherent signals. Because all signals generated are coherent and have a repetitive determined phase relationship with each other, it is possible to combine these signals interferometrically to produce a signal that is related to the relative phase of the two sets of signals.

By controlling the relative repetitive frequencies of the two generators, the point in time at which the two sets interfere can be scanned sequentially with a scanning speed determined by the difference in the two frequencies. This can be used as the basis for a system that scans repeatedly through a section of a target. Furthermore, the difference between the repetitive frequencies of the discrete coherent sets can be such that high scanning rates can be achieved. By combining this electronic based high speed scanning with a conventional lower speed scan in an orthogonal direction, two dimensional high speed imaging can be achieved and therefore this system constitutes a real-time non-invasive tomographic system.

Figure 1:
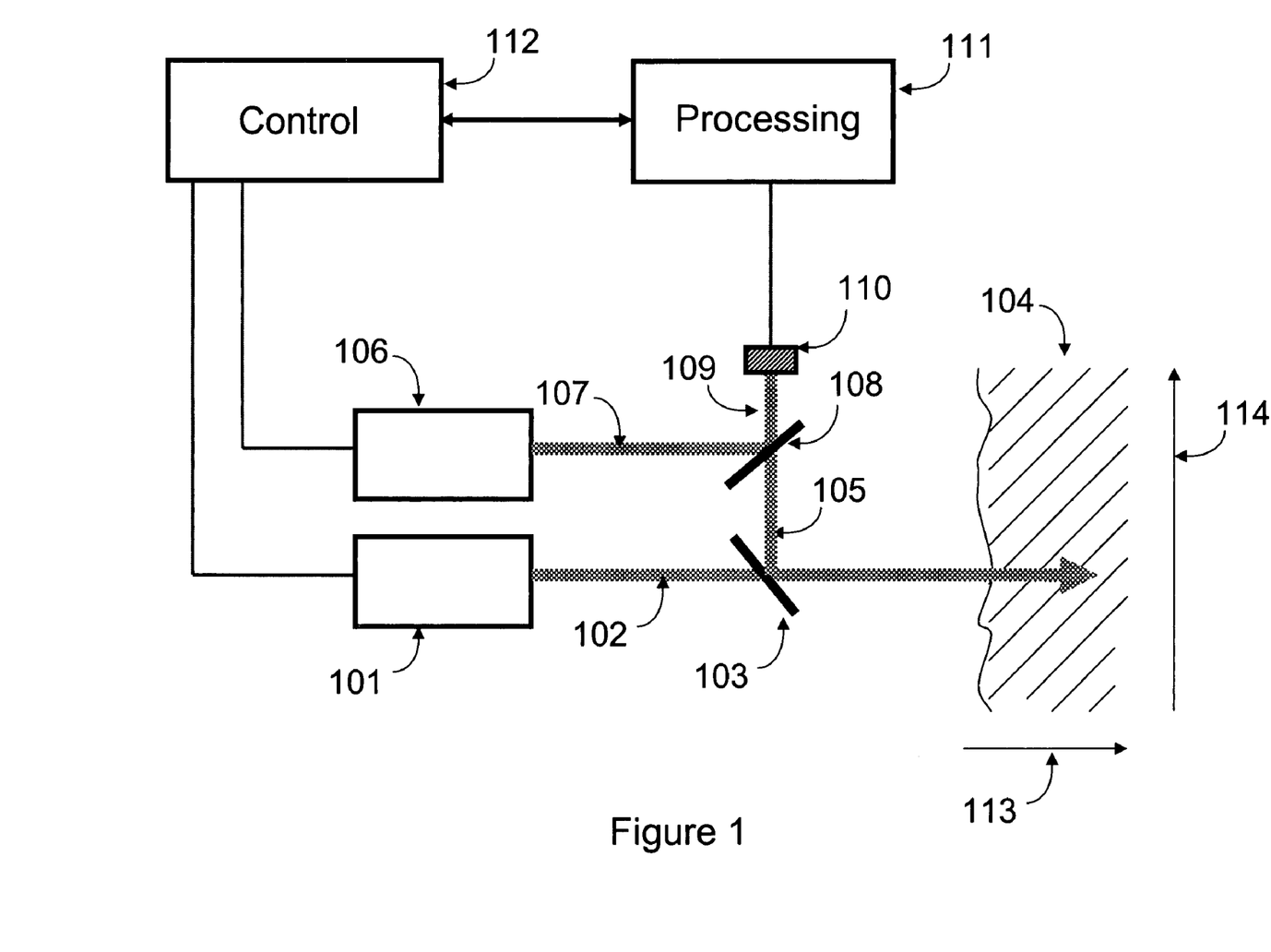
FIG. 1 is an illustration of the real-time imaging and analysis system according to the invention.

As illustrated in FIG. 1, the first generator 101 outputs a set of discrete coherent signals 102 that is applied to a target 104 to be imaged or analyzed. At least part of the set of discrete coherent signals, applied to the target is reflected or scattered back and redirected by a signal steering element 103 to a signal combining element 108.

The part of the set of discrete coherent signals directed to the combining element 108 by the steering element 103 is referred to as the captured signal 105 and because the strength of the signal reflected or scattered back from any point in the target is dependent on the characteristics of the target at that point, this captured signal contains information contributing to an image of the target.

The second generator 106 outputs a second set of discrete coherent signals, called the reference signal 107 that is also applied to the combining element 108 where it is combined interferometrically with the captured signal 105. The resulting interferometric signal 109 is detected by a detector 110.

The detected signal is processed by an processing module 111 in conjunction with timing signals from the control module 112, which also controls repetitive discrete coherent signal generators 101 and 106. The resulting information constitutes a one dimensional scan of a segment of the target along the depth or horizontal axis 113 of the target. This scan can be achieved at a high rate, because it is based on electronic control signals.

This process is repeated at different locations along an axis orthogonal to the horizontal axis, referred to as the vertical axis 114. Scanning in this vertical axis can be at lower rates and accomplished by conventional electromechanical translational techniques. The sequence of scans thus acquired constitute a real-time image sequence which can be electronically analyzed in real-time.

A preferred embodiment of the invention is illustrated in and described with reference to FIG. 2 where a real-time sub-surface imaging and analysis system is shown. The system includes a first electronically pumped and mode-locked laser diode 201, whose output beam 202, (which in this case is a set of discrete coherent optical signals), consists of a broad band set of wavelengths or modes that have a repetitive phase relationship with each other; the output beam 202, is collimated by a first lens 203. The output beam 202 is passed through a first beam splitter 204, such as a polarization beam splitter, through a quarter wave plate 205 and a second lens 206, with a relatively long Rayleigh range, e.g. 1 mm, and focused in a target 207. At least part of the optical signal applied to the target is reflected or scattered back and captured by the second lens 206. Reflection or scattering occurs because of discontinuities, such as changes of material properties, defects or changes of refractive index. The captured signal passes through the quarter waveplate 205, back to the first beam-splitter 204, where at least part of the captured signal 208 is directed to a second beam-splitter 209.

A second electronically mode-locked laser diode 210, whose output 211 is collimated by a third lens 212 and is also applied to the second beam splitter 209, where it is combined interferometrically with the captured signal 208. The resulting interference signal is detected by first and second opto-electronic detectors 213 and 214 and processed by a processing module 215. A control module 216 controls the mode-locked operation of the laser diodes 201 and 210 and also provides timing information to the processing module 215. The processing module combines this timing information with the detected interference signals to compute intensity as a function of depth within the target, which constitutes a one dimensional scan of the target. A single opto-electronic detector may be used. An advantage of using a first and a second opto-electronic detector is that it provides a means to suppress noise by exploiting the complementary nature of the signals and having them detected differentially.

Figure 2:
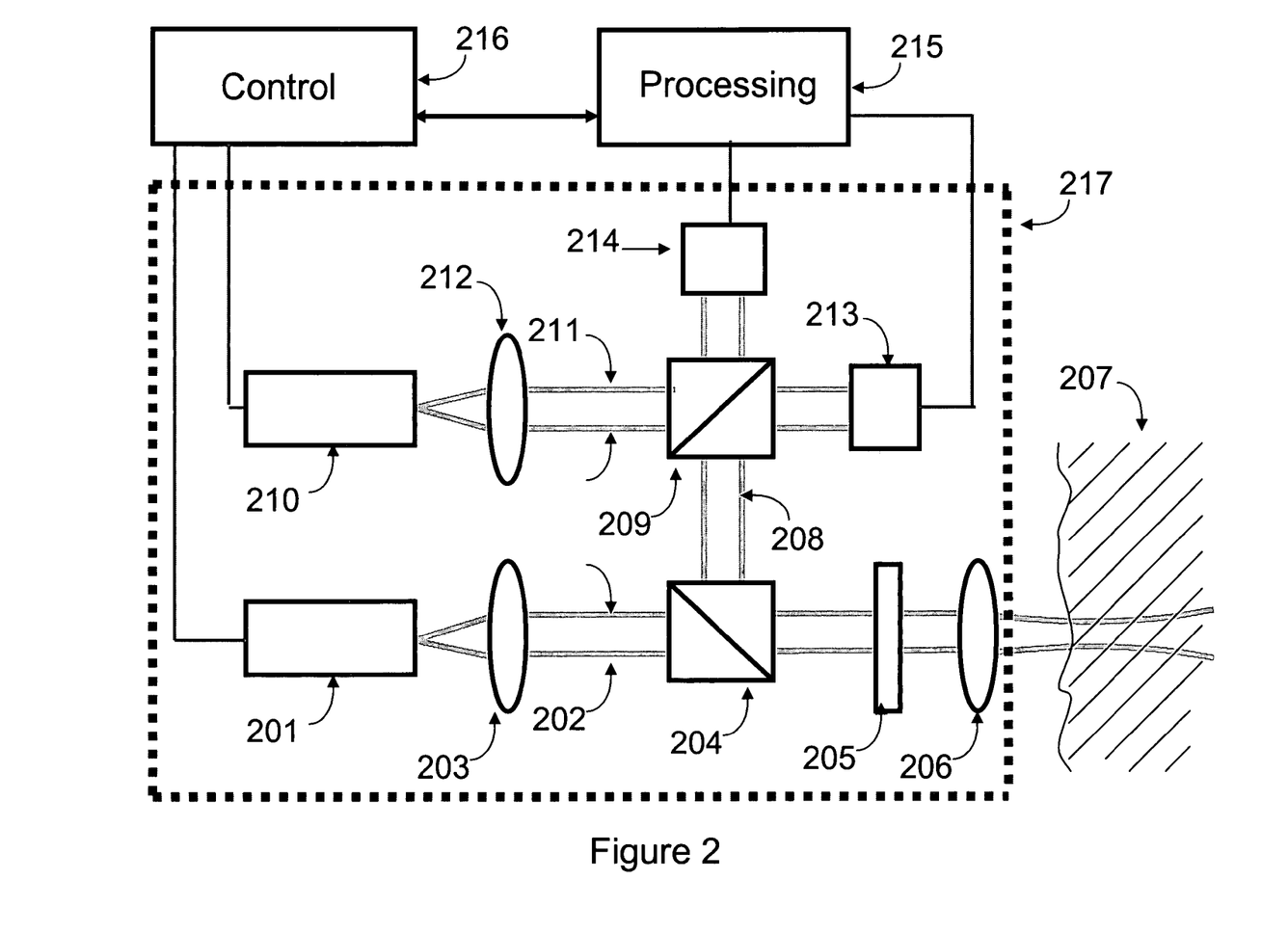
FIG. 2 is an illustration of a preferred embodiment of the invention.

The optical components, 201, 203, 204, 205, 206, 209, 210, 212, 213 and 214, enclosed by the dashed box 217 in FIG. 2, do not involve any moving parts and can be assembled in a compact manner on an optical micro-bench. Use of a compact micro-bench facilitates vertical axis scanning with conventional electromechanical techniques.

The control module 216, along with the processing module 215, combine successive one dimensional scans to generate a two dimensional scan. The control module 216 also stores the scans and control parameters in non-volatile memory for display, for further analysis and future operation. The electronic high speed scanning technique enables a real-time non-invasive imaging system. The resulting images can be analyzed visually using a real time display monitor or analyzed electronically, for example, by comparing a current image with previously acquired images.

Figure 3:
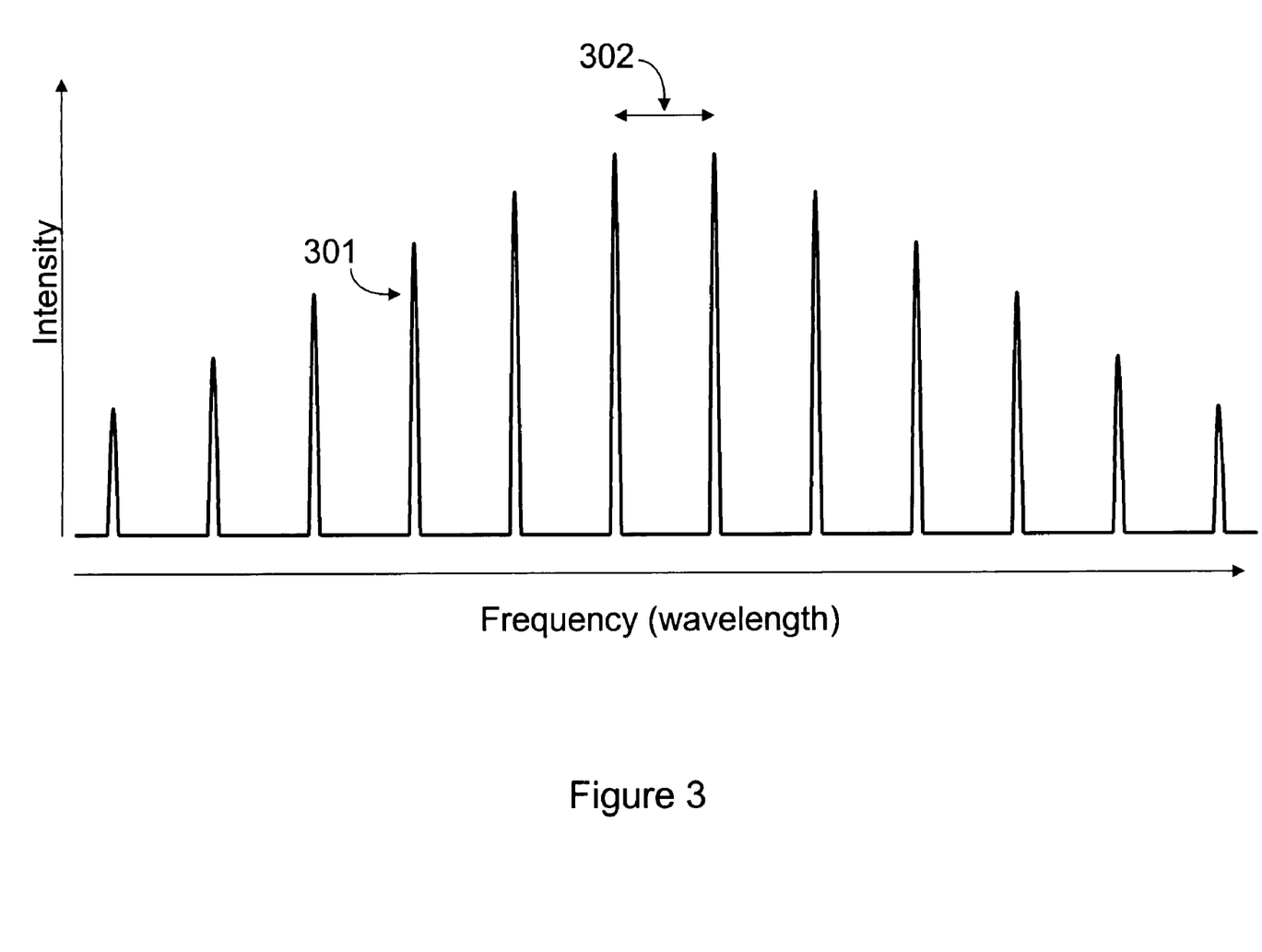
FIG. 3 is a frequency domain illustration of an output of a mode-locked laser optical source.

The output of a mode-locked laser diode is further illustrated in the frequency domain in FIG. 3 and consists of a set of modes, one of which is 301, which are separated from each other by a constant frequency difference 302. This frequency difference (delta_F) is related to the length of the laser diode according to the relationship delta_F=c/(2nL) where c is the speed of light, n is the refractive index of the lasing material and L is the length of the laser diode cavity.

Mode-locking is achieved by modulating the laser diode at a frequency equal to or harmonically related to the frequency delta_F. The output 202 of the laser diode 201, of FIG. 2, referred to as the probe signal, is illustrated in the time domain in FIG. 4, where it is shown as a pulse train 401 with a repetition period 403, (T1) which is the reciprocal of its repetition frequency delta_F1. The output of the second laser diode 210, of FIG. 2, is shown as the pulse train 402 with a repetition period 404, (T2) which is the reciprocal of its frequency delta_F2.

Figure 4:
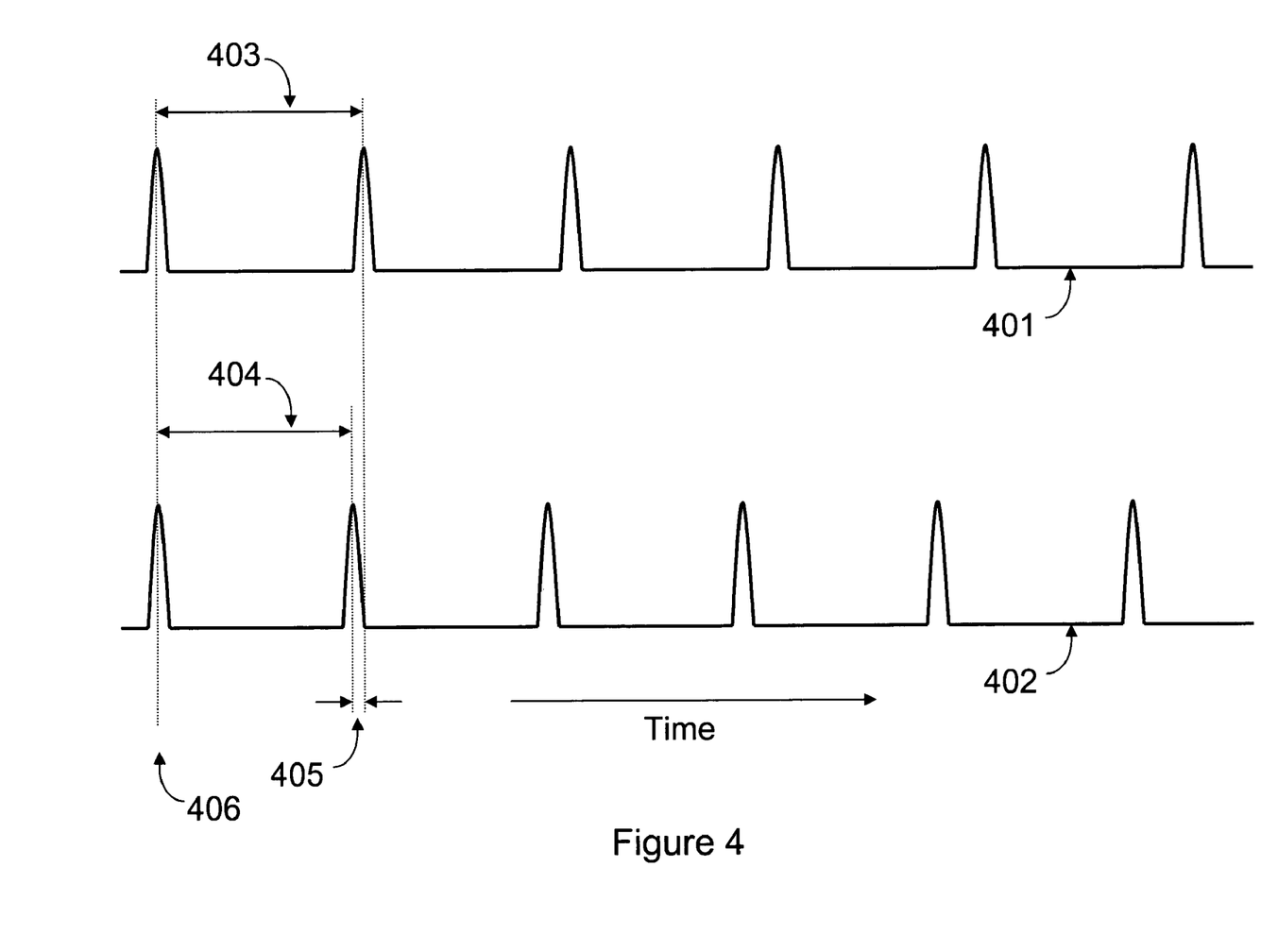
FIG. 4 is a time domain illustration of the outputs of mode-locked laser optical sources.

The difference between the two periods 405 corresponds to the difference between the two frequencies delta_F1 and delta_F2 and is referred to as a frequency offset. Pulses from the two pulse trains go from being aligned in time, as shown at point 406, to a systematic increase in misalignment until they come back into alignment. The frequency with which pulses come back into alignment is related to the frequency offset. The actual temporal relative alignment of the two pulse trains is referred to as their coherence phase offset.

When the captured signal 208 is combined with the reference signal 211, an interference signal will only exist when the captured signal is substantially aligned in time with the reference pulse. Since the reference and captured signals have different pulse frequencies, at any given time this alignment will correspond to only the optical signal reflected or scattered from a particular depth in the target.

Thus, having a frequency offset between the reference and probe signals has the effect of selectively discriminating in favor of detecting a signal reflected or scattered from different depths in the target at different times. This effectively provides an electronic method of scanning in depth (or along the horizontal axis), with the advantage of having no moving parts. The range of the depth or horizontal axis scan corresponds to the optical path length of the laser cavity. A full scan occurs with a frequency corresponding to the frequency offset 405.

The optical system 217 in FIG. 2 can then be translated in a direction perpendicular to the horizontal axis by conventional electromechanical techniques, to provide a two dimensional scan of the target.

The control module 216 in FIG. 2 generates the electronic signals to mode-lock both laser diodes 201 and 210 and provides a signal representing the frequency off set between them to the processing module 215. This signal represents the coherence phase offset between the reference and probe signals. This allows the processing module 215 to determine from what depth in the target the detected interferomatric signal was reflected or scattered.

A frequency offset between the two mode-locked lasers of the order of 15 KHz, allows for depth or horizontal scan rates that are compatible with video horizontal scan rates. This also allows corresponding wavelengths from the sets of wavelengths output by the two mode-locked lasers to have substantially the same wavelength values (Each pair is incrementally offset by 15 KHz). Frequencies other than 15 KHz are also usable.

Figure 5:
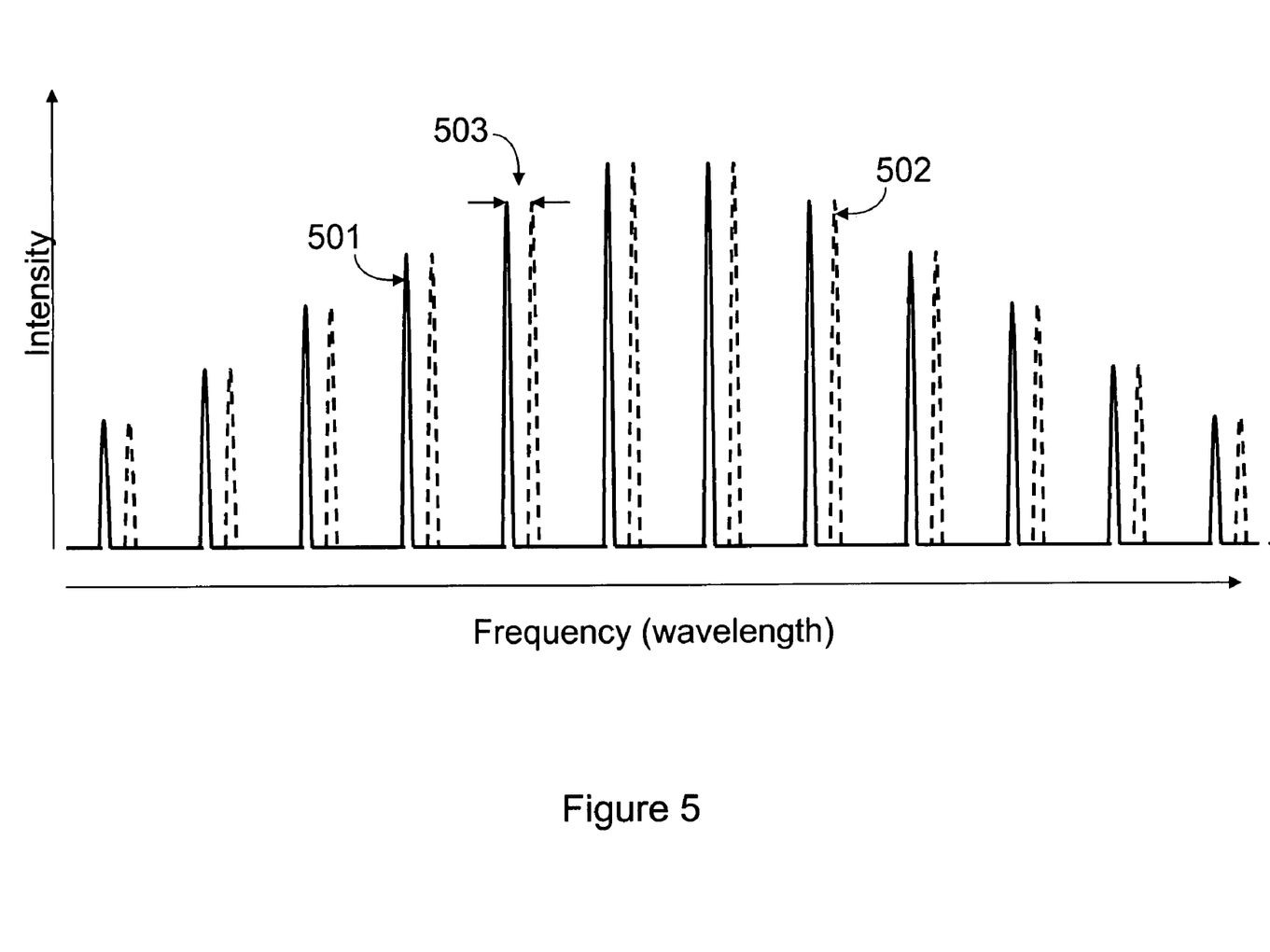
FIG. 5 is a frequency domain illustration of outputs of two mode-locked laser optical sources.

The two wavelength sets can optionally have a frequency offset, that is substantially the same for all corresponding wavelengths from the two sets. In FIG. 5, where the output of two mode-locked lasers are illustrated in the frequency domain and consists of a first of modes, one of which is 501, and a second set of modes, one of which is 502. (The second set of modes or wavelengths is illustrated by dashed lines.) These are offset by a frequency offset that is substantially the same for all corresponding modes (or wavelengths) of the two sets. This offset enables more sophisticated signal detection techniques, which includes but is not limited to coherent heterodyne techniques.

In an alternative embodiment, depth scanning can be accomplished by varying the temporal relationship between the captured scattered signal and the reference signal by modifying the coherence phase offset between the first and second mode-locked lasers. This can be done by, for example, having both lasers mode-locked at substantially the same frequency and varying the phase relation between RF (radio frequency) signals electronically mode-locking the lasers.

Figure 6:
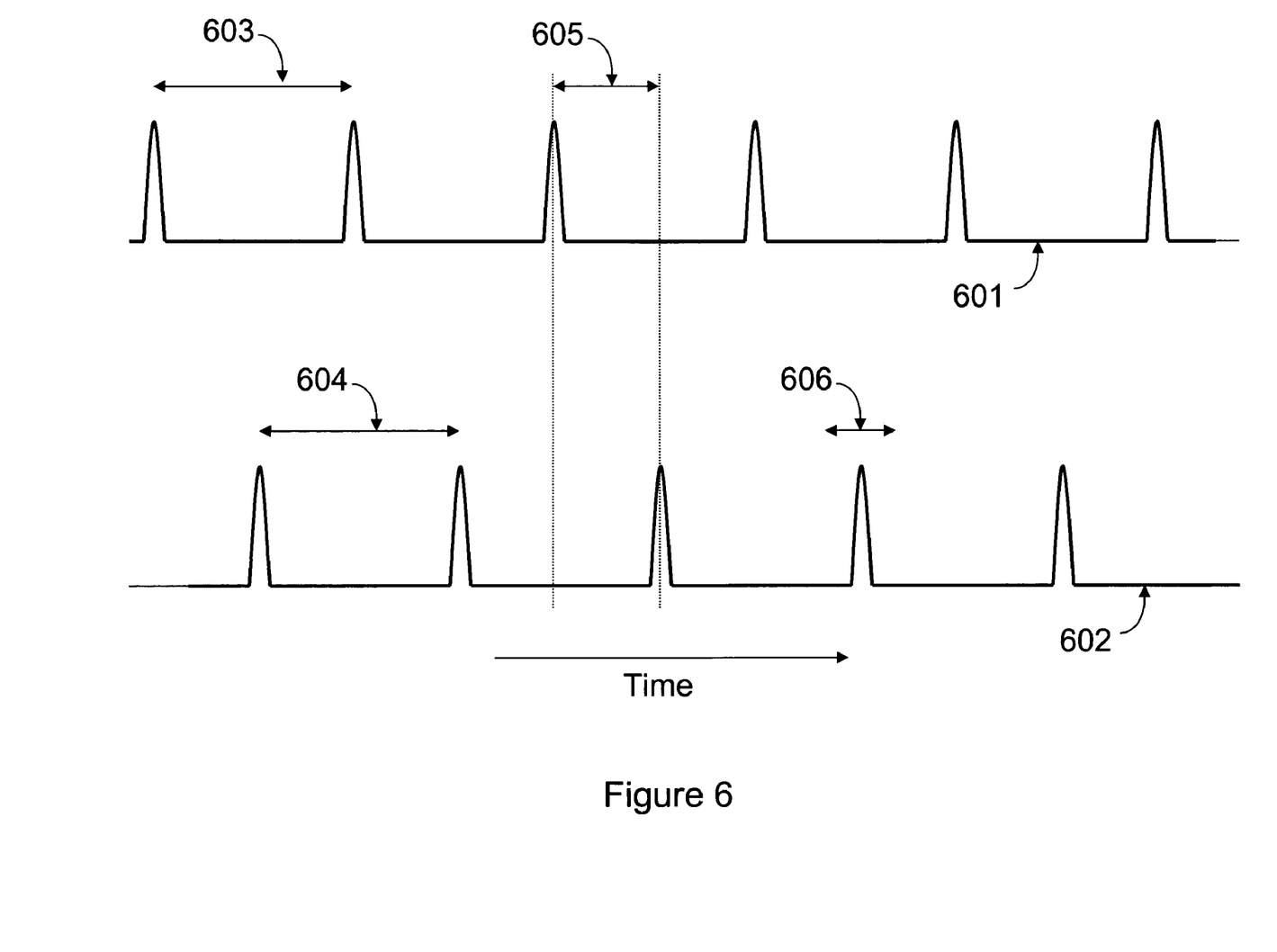
FIG. 6 is an alternate time domain illustration of the outputs of mode-locked laser sources.

Typical outputs of the lasers in such an embodiment are illustrated in FIG. 6, where the first laser output 601 and the second laser output 602 have substantially the same repetition rate indicated by the periods 603 and 604. The phase coherence between the two pulse trains 605 is aligned so the pulse trains are substantially 180 degrees out of phase when the signals are combined interferometrically.

Scanning is accomplished by varying this phase relationship by an amount, for example, indicated by 606. The scanning frequency is determined by the frequency with which the phase coherence is modulated. The scanning range is determined by the magnitude of the phase coherence variation 606.

It is understood that the above description is intended to be illustrative and not restrictive. Many of the features have functional equivalents that are intended to be included in the invention as being taught.

For example, the mode-locked laser could be optically pumped, it could be a solid state laser, such as a Cr:LiSAF laser optically pumped by a diode laser and it could be passively mode locked by a Kerr lens or a semiconductor saturable absorber mirror. Gain switched optical sources, with optical feedback to lock modes may also be used. For purposes of this invention, mode-locked lasers will include gain switched sources.

The scanned information may be analyzed for other than imaging purposes, for example, it may be used to map discontinuities. Such discontinuities include defects and refractive index changes. The discontinuity map may be analyzed to provide characteristic information about the target, such as concentration of particular constituent analytes. Depth scans at multiple entry points can be averaged to further analyze these characteristics. For purposes of this invention, imaging will include analysis in general.

The technique is not restricted to discrete coherent optical signals. The invention could also be implemented using generators of discrete coherent acoustic signals or using discrete coherent RF signals.

Other examples will be apparent to persons skilled in the art. The scope of this invention should therefore not be determined with reference to the above description, but instead should be determined with reference to the appended claims, along with the full scope of equivalents to which such claims are entitled.

What is claimed is:

1. A method for sub-surface imaging a target comprising:
generating at least one set of discrete coherent signals;
applying at least part of said set of discrete coherent signals to the target to be analyzed;
capturing and steering at least part of said set of discrete coherent signals (captured signal) returned from the target;
combining the captured signal with a reference signal;
modifying the temporal coherence phase relationship between the captured and reference signals;
detecting the interference signal between the captured and reference signals;
analyzing the detected interference signals at multiple temporal relationships; and
generating an image of the target.

2. The method of claim 1, wherein the set of discrete coherent signals is a set of discrete coherent optical signals generated by a first mode-locked laser.

3. The method of claim 2, wherein the mode-locked laser is a mode-locked semiconductor laser.

4. The method of claim 2, wherein the mode-locked laser is electronically pumped.

5. The method of claim 2, wherein the mode-locked laser is optically pumped by a semiconductor laser diode.

6. The method of claim 2, wherein the mode-locked laser is a Cr:LiSAF laser.

7. The method of claim 2, wherein mode-locking is achieved electronically.

8. The method of claim 2, wherein mode-locking is achieved passively.

9. The method of claim 8, wherein passive mode-locking is achieved by means of a Kerr lens.

10. The method of claim 8, wherein passive mode-locking is achieved by means of a semiconductor saturable absorber mirror.

11. The method of claim 1, wherein at least a part of the set of discrete coherent signals is focused in the target to be analyzed by means of a lens with a long Rayleigh focus range.

12. The method of claim 11, wherein the Rayleigh range is of the order of one or more millimeters.

13. The method of claim 1, wherein part of the generated the set of discrete coherent signals is returned by reflective properties of the target.

14. The method of claim 1, wherein part of the generated set of discrete coherent signals is returned by discontinuities in the target.

15. The method of claim 14, wherein the discontinuities in the target are caused by changes of refractive index.

16. The method of claim 1, wherein the captured signal is captured by the focusing lens.

17. The method of claim 1, wherein the captured signal is separated by means of a polarization separator.

18. The method of claim 1, wherein the captured signal is combined with a reference signal generated by a second mode-locked laser.

19. The method of claim 18, wherein the second mode-locked laser has a mode locking frequency offset from the first mode-locked laser.

20. The method of claim 18, wherein the second mode-locked laser has the same wavelength range and mode locking frequency as the first mode-locked laser.

21. The method of claim 18, wherein the second mode locked laser has substantially the same wavelength values as the first mode-locked laser.

22. The method of claim 18, wherein the second mode-locked laser has wavelength values offset from the wavelength values of the first mode-locked laser by an offset that is substantially the same for all corresponding wavelengths.

23. The method of claim 18, wherein the coherence phase of the second mode-locked laser may be phase offset from the coherence phase of the first mode-locked laser.

24. The method of claim 1, wherein the temporal relationship between the captured signal and the reference signal is modified by modifying the coherence phase offset between the first and second mode-locked lasers.

25. The method of claim 1, wherein the temporal relationship between the captured signal and the reference signal is modified by means of the frequency offset between the first and second mode-locked lasers.

26. The method of claim 25, wherein the frequency offset corresponds to a horizontal video scanning frequency.

27. The method of claim 1, wherein the temporal relationship between the captured signal and the reference signal is modified by modifying the relative optical path difference between the captured and reference signals.

28. The method of claim 1, wherein the captured signal and the reference signal are combined interferometrically.

29. The method of claim 1, wherein the interference signal between the captured and reference signals is detected by means of an opto-electronic detector.

30. The method of claim 1, wherein the interference signal between the captured and reference signals is detected differentially by means of two opto-electronic detectors.

31. The method of claim 1, wherein the interference signals are detected by means of at least one opto-electronic detector at multiple temporal relationships between the captured and reference signals.

32. The method of claim 1, wherein the detected signals are combined with electronic signals aligned with the coherence phase of the reference signal.

33. The method of claim 1, wherein the detected signals are analyzed by means of combining information from detected signals at at least two temporal relationships between the captured and reference signals.

34. The method of claim 33, wherein the detected signals are analyzed to determine the detected signals as a function of the temporal relationships between the captured and reference signals.

35. The method of claim 34, wherein the detected signals as a function of the temporal relationships between the captured and reference signals are analyzed by an electronic processing system to generate an image of the target to be analyzed.

36. The method of claim 1, wherein an electronic control system coordinates the temporal relationships between the captured and reference signals, electronic signals aligned with the coherence phase of the reference signal, the detected signals and the processing system.

37. The method of claim 1, wherein the electronic control system stores control parameters in electronic memory.

38. The method of claim 1, wherein the electronic control system stores processed information in electronic memory.

39. The method of claim 1, wherein the set of discrete coherent signals is applied successively to multiple entry points of the target to be analyzed.

40. The method of claim 39, wherein the scans generated successively at multiple entry points of the target are averaged.

41. The method of claim 1, wherein a two dimensional image of the target is generated.

42. The method of claim 1, wherein images are generated continuously.

43. The method of claim 1, wherein images are displayed continuously.

44. The method of claim 1, wherein images are analyzed visually.

45. The method of claim 1, wherein images are analyzed electronically.

46. The method of claim 1, wherein the set of discrete coherent signals is a set of acoustic signals.

47. The method of claim 1, wherein the set of discrete coherent signals is a set of RF signals.

48. A system for sub-surface imaging a target comprising:
generating at least one set of discrete coherent signals;
applying at least part of said set of discrete coherent signals to the target to be analyzed;

capturing and steering at least part of said set of discrete coherent signals (captured signal) returned from the target;

combining the captured signal with a reference signal;

modifying the temporal coherence phase relationship between the captured and reference signals;

detecting the interference signal between the captured and reference signals;

analyzing the detected interference signals at multiple temporal relationships; and generating an image of the target.

49. An apparatus for sub-surface imaging a target comprising:

means for generating at least one set of discrete coherent signals;

means for applying at least part of said set of discrete coherent signals to the target to be analyzed;

means for capturing and steering at least part of said set of discrete coherent signals (captured signal) returned from the target;

means for combining the captured signal with a reference signal;

means for modifying the temporal coherence phase relationship between the captured and reference signals;

means for detecting the interference signal between the captured and reference signals;

means for analyzing the detected interference signals at multiple temporal relationships; and means for generating an image of the target.

50. The apparatus of claim 49, wherein the set of discrete coherent signals is a set of discrete coherent optical signals generated by a first mode-locked laser.

51. The apparatus of claim 50, wherein the mode-locked laser is a mode-locked semiconductor laser.

52. The apparatus of claim 50, wherein the mode-locked laser is electronically pumped.

53. The apparatus of claim 50, wherein the mode-locked laser is optically pumped by a semiconductor laser diode.

54. The apparatus of claim 50, wherein the mode-locked laser is a Cr:LiSAF laser.

55. The apparatus of claim 50, wherein mode-locking is achieved electronically.

56. The apparatus of claim 50, wherein mode-locking is achieved passively.

57. The apparatus of claim 56, wherein passive mode-locking is achieved by means of a Kerr lens.

58. The apparatus of claim 56, wherein passive mode-locking is achieved by means of a semiconductor saturable absorber mirror.

59. The apparatus of claim 56, wherein at least a part of the set of discrete coherent signals is focused in the target to be analyzed by means of a lens with a long Rayleigh focus range.

60. The apparatus of claim 59, wherein the Rayleigh range is of the order of one or more millimeters.

61. The apparatus of claim 49, wherein part of the generated the set of discrete coherent signals is returned by reflective properties of the target.

62. The apparatus of claim 49, wherein part of the generated set of discrete coherent signals is returned by discontinuities in the target.

63. The apparatus of claim 62, wherein the discontinuities in the target are caused by changes of refractive index.

64. The apparatus of claim 49, wherein the captured signal is captured by the focusing lens.

65. The apparatus of claim 49, wherein the captured signal is separated by means of a polarization separator.

66. The apparatus of claim 49, wherein the captured signal is combined with a reference signal generated by a second mode-locked laser.

67. The apparatus of claim 66, wherein the second mode-locked laser has a mode locking frequency offset from the first mode-locked laser.

68. The apparatus of claim 66, wherein the second mode-locked laser has the same wavelength range and mode locking frequency as the first mode-locked laser.

69. The apparatus of claim 66, wherein the second mode locked laser has substantially the same wavelength values as the first mode-locked laser.

70. The apparatus of claim 66, wherein the second mode-locked laser has wavelength values offset from the wavelength values of the first mode-locked laser by an offset that is substantially the same for all corresponding wavelengths.

71. The apparatus of claim 66, wherein the coherence phase of the second mode-locked laser may be phase offset from the coherence phase of the first mode-locked laser.

72. The apparatus of claim 49, wherein the temporal relationship between the captured signal and the reference signal is modified by modifying the coherence phase offset between the first and second mode-locked lasers.

73. The apparatus of claim 49, wherein the temporal relationship between the captured signal and the reference signal is modified by means of the frequency offset between the first and second mode-locked lasers.

74. The apparatus of claim 73, wherein the frequency offset corresponds to a horizontal video scanning frequency.

75. The apparatus of claim 49, wherein the temporal relationship between the captured signal and the reference signal is modified by modifying the relative optical path difference between the captured and reference signals.

76. The apparatus of claim 49, wherein the captured signal and the reference signal are combined interferometrically.

77. The apparatus of claim 49, wherein the interference signal between the captured and reference signals is detected by means of an opto-electronic detector.

78. The apparatus of claim 49, wherein the interference signal between the captured and reference signals is detected differentially by means of two opto-electronic detectors.

79. The apparatus of claim 49, wherein the interference signals are detected by means of at least one opto-electronic detector at multiple temporal relationships between the captured and reference signals.

80. The apparatus of claim 49, wherein the detected signals are combined with electronic signals aligned with the coherence phase of the reference signal.

81. The apparatus of claim 49, wherein the detected signals are analyzed by means of combining information from detected signals at at least two temporal relationships between the captured and reference signals.

82. The apparatus of claim 81, wherein the detected signals are analyzed to determine the detected signals as a function of the temporal relationships between the captured and reference signals.

83. The apparatus of claim 82, wherein the detected signals as a function of the temporal relationships between the captured and reference signals are analyzed by an electronic processing system to generate an image of the target to be analyzed.

84. The apparatus of claim 49, wherein an electronic control system coordinates the temporal relationships between the captured and reference signals, electronic signals aligned with the coherence phase of the reference signal, the detected signals and the processing system.

85. The apparatus of claim 49, wherein the electronic control system stores control parameters in electronic memory.

86. The apparatus of claim 49, wherein the electronic control system stores processed information in electronic memory.

87. The apparatus of claim 49, wherein the set of discrete coherent signals is applied successively to multiple entry points of the target to be analyzed.

88. The apparatus of claim 87, wherein the scans generated successively at multiple entry points of the target are averaged.

89. The apparatus of claim 49, wherein a two dimensional image of the target is generated.

90. The apparatus of claim 49, wherein images are generated continuously.

91. The apparatus of claim 49, wherein images are displayed continuously.

92. The apparatus of claim 49, wherein images are analyzed visually.

93. The apparatus of claim 49, wherein images are analyzed electronically.

94. The apparatus of claim 49, wherein the set of discrete coherent signals is a set of acoustic signals.

95. The apparatus of claim 49, wherein the set of discrete coherent signals is a set of RF signals.

* * * * *